United States Patent
Reghabi et al.

(10) Patent No.: US 7,247,138 B2
(45) Date of Patent: *Jul. 24, 2007

(54) REUSABLE ANALYTE SENSOR SITE AND METHOD OF USING THE SAME

(75) Inventors: Bahar Reghabi, Marina Del Rey, CA (US); Rajiv Shah, Rancho Palos Verdes, CA (US); Eunjoo Jin, Los Angeles, CA (US); Rebecca Gottlieb, Culver City, CA (US); Michael E. Miller, Culver City, CA (US); Nannette M. Van Antwerp, Valencia, CA (US); Bradley J. Enegren, Moorpark, CA (US); William P. Van Antwerp, Valencia, CA (US); John J. Mastrototaro, Los Angeles, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 870 days.

This patent is subject to a terminal disclaimer.

(21) Appl. No.: 10/365,279

(22) Filed: Feb. 12, 2003

(65) Prior Publication Data

US 2003/0220552 A1 Nov. 27, 2003

Related U.S. Application Data

(60) Continuation-in-part of application No. 10/028,070, filed on Dec. 21, 2001, which is a division of application No. 09/566,027, filed on May 8, 2000, now Pat. No. 6,368,274.

(60) Provisional application No. 60/141,935, filed on Jul. 1, 1999.

(51) Int. Cl.
 *A61B 5/00* (2006.01)
 *A61B 19/00* (2006.01)
 *A61M 5/32* (2006.01)

(52) U.S. Cl. ............... 600/365; 600/309; 600/300; 604/174; 604/175; 128/899

(58) Field of Classification Search ............ 600/309, 600/300, 345–366; 424/422–426; 604/174, 604/175, 891.1, 890.1; 128/899
See application file for complete search history.

(56) References Cited

U.S. PATENT DOCUMENTS 3,818,515 A * 6/1974 Neville ................... 623/9

(Continued)

FOREIGN PATENT DOCUMENTS

WO 8101794 7/1981

(Continued)

*Primary Examiner*—Robert L. Nasser
*Assistant Examiner*—Navin Natnithithadha

(57) ABSTRACT

A reusable analyte sensor site for use with a replaceable analyte sensor for determining a level of an analyte includes a site housing material and a resealable insertion site coupled to one end of the site housing material. Preferably, the site housing material is formed to have an interior cavity with an opening. The site housing material is selected to promote tissue ingrowth and vascularization, and yet be free of tissue ingress. Also, the site housing material permits the analyte to pass through the site housing material to the interior cavity to permit measurement by the replaceable analyte sensor. The resealable insertion site provides a for inserting the replaceable analyte sensor into the interior cavity of the site housing material.

36 Claims, 6 Drawing Sheets

U.S. PATENT DOCUMENTS

| | | |
|---|---|---|
| 4,140,963 A | 2/1979 | Rao et al. |
| 4,240,438 A | 12/1980 | Updike et al. |
| 4,533,349 A * | 8/1985 | Bark .......................... 604/174 |
| 4,757,022 A | 7/1988 | Shults et al. |
| 4,986,271 A | 1/1991 | Wilkins |
| 4,994,167 A | 2/1991 | Shults et al. |
| 5,324,518 A | 6/1994 | Orth et al. |
| 5,431,160 A | 7/1995 | Wilkins |
| 5,476,776 A | 12/1995 | Wilkins |
| 5,651,767 A | 7/1997 | Schulman et al. |
| 6,368,274 B1 * | 4/2002 | Van Antwerp et al. ...... 600/365 |
| 6,459,917 B1 * | 10/2002 | Gowda et al. .............. 600/345 |
| 7,044,911 B2 * | 5/2006 | Drinan et al. ............... 600/300 |
| 2002/0055673 A1 * | 5/2002 | Van Antwerp et al. ...... 600/365 |
| 2004/0143173 A1 * | 7/2004 | Reghabi et al. ............. 600/365 |

FOREIGN PATENT DOCUMENTS

| | | |
|---|---|---|
| WO | 9207525 | 5/1992 |
| WO | 9719188 | 5/1997 |

* cited by examiner

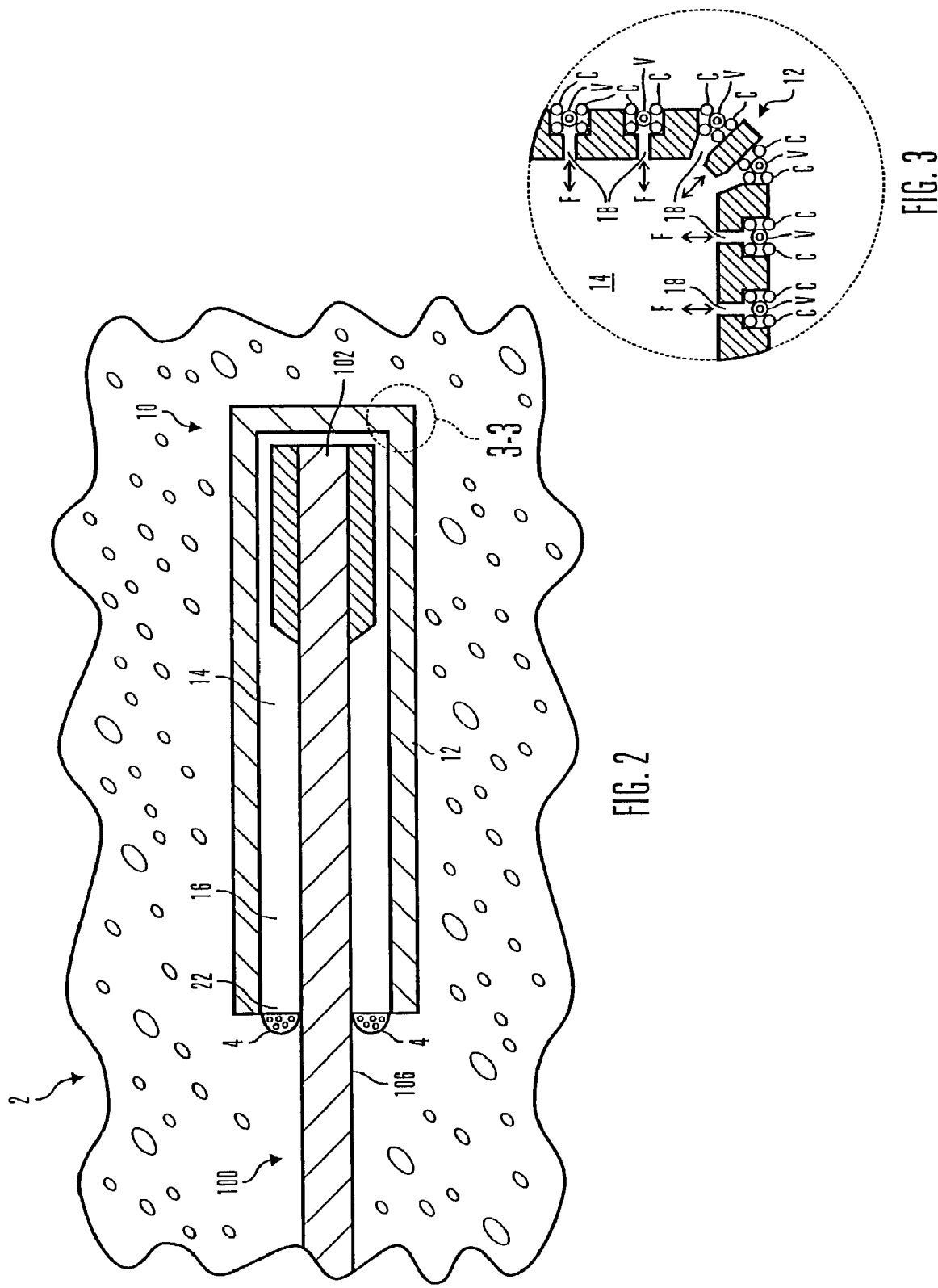

US 7,247,138 B2

REUSABLE ANALYTE SENSOR SITE AND METHOD OF USING THE SAME

RELATED APPLICATIONS

This application is a continuation-in-part of U.S. patent application Ser. No. 10/028,070 filed Dec. 21, 2001 and entitled "Reusable Analyte Sensor Site and Method of Using the Same," which is a divisional of U.S. patent application Ser. No. 09/566,027 filed May 8, 2000 and entitled "Reusable Analyte Sensor Site and Method of Using the Same," now U.S. Pat. No. 6,368,274 issued Apr. 9, 2002, which claims priority on U.S. Provisional Application Ser. No. 60/141,935 filed Jul. 1, 1999 and entitled "Reusable Analyte Sensor Site and Method of Using the Same," all of which are herein specifically incorporated by reference.

FIELD OF THE INVENTION

This invention relates to reusable analyte sensor sites for use with replaceable, long term implantable anlayte sensors, in particular embodiments, to reusable glucose sensor sites for use with replaceable, long term glucose sensors.

BACKGROUND OF THE INVENTION

Over the years, bodily characteristics have been determined by obtaining a sample of bodily fluid. For example, diabetics often test for blood glucose levels with a blood glucose meter. Traditional blood glucose determinations have utilized a painful finger prick using a lancet to withdraw a small blood sample that is used by the blood glucose meter. This results in discomfort from the lancet as it contacts nerves in the subcutaneous tissue. The pain of lancing and the cumulative discomfort from multiple needle pricks is a strong reason why patients fail to comply with a medical testing regimen used to determine a change in characteristic over a period of time. In addition, these blood glucose meters are only designed to provide data at discrete points and do not provide continuous data to show the variations in the characteristic between testing times.

A variety of subcutaneous electrochemical sensors for use with monitors have been developed for detecting and/or quantifying specific agents or compositions in a patient's blood. For instance, glucose sensors have been developed for use in obtaining an indication of blood glucose levels in a diabetic patient. Such readings are useful in monitoring and/or adjusting a treatment regimen which typically includes the regular administration of insulin to the patient. Thus, blood glucose readings from the monitor improve medical therapies with semi-automated medication infusion pumps of the external type, as generally described in U.S. Pat. Nos. 4,562,751; 4,678,408; and 4,685,903, which are herein incorporated by reference. Typical thin film sensors are described in commonly assigned U.S. Pat. Nos. 5,390,671; 5,391,250; 5,482,473; and 5,586,553, which are incorporated by reference herein. However, the thin film subcutaneous glucose sensor must be changed every few days to prevent infection. Also, due to the small size of this sensor to minimize pain on insertion under the skin, the enzymes on the sensor wear out relatively quickly and require regular replacement. In addition, the user must carry around external hardware connected or linked to the sensor. Thus, although subcutaneous sensors provide an improvement over conventional test strips, they still require frequent changes.

Long term implanted glucose sensors have been proposed that can stay in the body for long periods of time, such as weeks and months. These long term implanted glucose sensors are particularly well adapted for use with automated implantable medication infusion pumps, as generally described in U.S. Pat. No. 4,573,994, which is herein incorporated by reference. The long term glucose sensor would obviate the need for frequent replacement of sensors and the need to carry around a large amount of external equipment. However, the long term glucose sensor is typically placed in the superior vena cava of the patient's body, and the insertion and placement of the long term sensor in this location is quite invasive to the body and requires much effort by an attending physician. As a result, removal and replacement of long term sensors in the superior vena cava is difficult.

Long term glucose sensors may be adapted for insertion and placement in locations that are less invasive to the body and require less effort by the attending physician, such as the peritoneal, subcutaneous, and/or adipose tissue of the patient's body. For example, an outer covering may be formed around the long term sensor, and the long term sensor formed with the outer covering may then be placed into the peritoneal, subcutaneous, or adipose tissue of the patient's body. After insertion, the long term sensor would not be usable for a period of time until the body heals and vascularizes the implanted long term sensor. Thus, each time a long term sensor formed with an outer covering is replaced, the body must re-vascularize the replaced sensor. Another drawback to long term sensors is the development of scar tissue at the insertion site that encapsulates the implanted sensor formed with the outer covering. Therefore, materials must be carefully selected to promote vascularization and not encapsulation. This requires careful construction of the outer covering for the long term sensor, which increases costs and may further delay the period of time before a newly implanted sensor may be used. Further, extensive surgery may be required to cut through the scar tissue and remove the implanted sensor, thus rendering the insertion site unusable for implantation of a replacement sensor. Accordingly, to minimize and/or eliminate the delay due to re-vascularization and the need for extensive surgery due to encapsulation, it would be desirable to develop a reusable sensor insertion site for use with a replaceable sensor.

SUMMARY OF THE DISCLOSURE

It is an object of an embodiment of the present invention to provide an improved reusable analyte sensor site, which obviates for practical purposes, the above mentioned limitations.

According to an embodiment of the invention, a reusable analyte sensor site for use with a replaceable analyte sensor for determining a level of an analyte includes a site housing. Preferably, the site housing material is formed to have an interior cavity with an opening and a conduit that is connected to the opening of the interior cavity to provide access to the interior cavity. The site housing material is selected to promote tissue ingrowth and vascularization, and yet be free of tissue ingress. Also, the site housing material permits the analyte to pass through the site housing material to the interior cavity to permit measurement by the replaceable analyte sensor. In addition, the conduit has a predetermined length to inhibit trauma and encapsulation of tissue occurring at the conduit, which is associated with placing the replaceable analyte sensor in the interior cavity of the site housing, from interfering with the tissue ingrowth and vascularization surrounding the interior cavity of the site housing material.

In particular embodiments, the conduit may have a length of at least 5 millimeters, and the site housing material may have a porosity in a range from 2 to 25 microns. Preferably, the site housing is for implantation into sub-dermal tissue and/or inter-peritoneal tissue. Also, the site housing material is selected from a group of materials consisting essentially of Teflon and Dacron. In addition, the site housing is chosen so that it will last for a period of time such that it can be used with two or more consecutive replaceable analyte sensors.

Preferred embodiments utilize a site housing material that passes glucose, and the replaceable analyte sensor is a glucose sensor. In other embodiments, the invention is embodied in a system that uses a replaceable analyte sensor with the reusable analyte sensor site. In alternative embodiments, the reusable analyte sensor site may be used with a replaceable infusion catheter for infusing a fluid into the body of a user. In further alternative embodiments, the reusable analyte sensor site may be used with a replaceable stimulator or pacing lead for delivering electrical pulses to selected areas in the body of the user.

In another embodiment of the present invention, a reusable analyte sensor site for use with a replaceable analyte sensor for determining a level of an analyte includes a site housing material. The site housing material is preferably formed to have an interior cavity with an opening. The site housing material is also selected to promote tissue ingrowth and vascularization, but be free of tissue ingress. Additionally, the site housing material permits fluid including the analyte to pass through the site housing material to the interior cavity to permit measurement by the replaceable analyte sensor. Further, the interior cavity has a predetermined size to inhibit stagnation of the fluid including the analyte within the interior cavity.

In particular embodiments, the site housing material may have a porosity in a range from 2 to 25 microns. The site housing is preferably for implantation into sub-dermal and/or inter-peritoneal tissue. Also, the site housing material may be selected from a group of materials consisting essentially of Teflon and Dacron. Further, the site housing material will last for a period of time such that it can be used with two or more consecutive replaceable analyte sensors.

Preferred embodiments utilize a site housing material that passes glucose, and the replaceable analyte sensor is a glucose sensor. In other embodiments, the invention is embodied in a system that uses a replaceable analyte sensor with the reusable analyte sensor site. In alternative embodiments, the reusable analyte sensor site may be used with a replaceable infusion catheter for infusing a fluid into the body of a user. In further alternative embodiments, the reusable analyte sensor site may be used with a replaceable stimulator or pacing lead for delivering electrical pulses to selected areas in the body of the user.

In yet another embodiment of the present invention, a reusable analyte sensor site for use with a replaceable analyte sensor for determining a level of an analyte in a patient includes a site housing material and a resealable insertion site. The site housing material is formed to have an interior cavity with an opening. Additionally, the site housing material is selected to promote tissue ingrowth and vascularization, but be free of tissue ingress. The site housing material also permits fluid including the analyte to pass through the site housing material to the interior cavity to permit measurement by the replaceable analyte sensor. The resealable insertion site is coupled to one end of the site housing material, and the replaceable analyte sensor is inserted through the resealable insertion site into the interior cavity of the site housing material.

In particular embodiments, the resealable insertion site includes a tube and a sealing member with a resealable opening. The tube is coupled to one end of the site housing material, and the tube is coupled between the site housing material and the sealing member. The replaceable analyte sensor is inserted through the resealable opening, and the resealable opening is sealed upon placement of the replaceable analyte sensor within the interior cavity of the site housing material. The sealing member may be a suture disc or a sewing cuff for attaching the tube to body tissue of the patient. In additional embodiments, the tube and the suture disc may be combined into an integral unit. In further embodiments, the sensor site may also include another suture disc coupled to the other end of the site housing material for attaching the other end of the site housing material to the body tissue of the patient.

In some embodiments, the resealable opening may be sealed using a compression seal. The tube may have a smaller size than the sealing member such that the tube compresses the sealing member within the tube and seals the resealable opening around the replaceable analyte sensor. Alternatively, the resealable insertion site may also include a ring that is placed over the sealing member to compress and seal the resealable opening around the replaceable analyte sensor. Further, a cross-cut may be formed in the sealing member at the resealable opening.

In other embodiments, the resealable opening may be sealed using a mechanical seal. The resealable insertion site may include a Touhy-Borst placed over the sensor to lock the replaceable analyte sensor into the resealable opening. Alternatively, the resealable insertion site may include a replaceable septum placed over the sensor and the resealable opening.

In further particular embodiments, the sensor site is adapted for connection to an injection site for delivering fluids into the site housing material. In still other particular embodiments, the interior cavity has a predetermined size to inhibit stagnation of the fluid including the analyte within the interior cavity.

Preferably, the site housing material is for implantation into inter-peritoneal tissue of the patient, and the resealable insertion site is for implantation into subcutaneous tissue of the patient. Additionally, the site housing material may be selected from a group of materials consisting essentially of polytetra fluoroethylene, porous polyurethane, porous silicone, and silicone foam. Also, the site housing material will last for a period of time such that it can be used with two or more consecutive replaceable analyte sensors.

Preferred embodiments utilize a site housing material that passes glucose, and the replaceable analyte sensor is a glucose sensor. In other embodiments, the invention is embodied in a system that uses a replaceable analyte sensor with the reusable analyte sensor site. In alternative embodiments, the reusable analyte sensor site may be used with a replaceable infusion catheter for infusing a fluid into the body of a user. In further alternative embodiments, the reusable analyte sensor site may be used with a replaceable stimulator or pacing lead for delivering electrical pulses to selected areas in the body of the user.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

FIG. 2 is a partial cross-sectional diagram of the reusable analyte sensor site as shown along the line 2-2 in FIG. 1.

FIG. 3 is an enlarged cross-sectional view of the reusable sensor site as shown within the circle 3-3 in FIG. 2.

DETAILED DESCRIPTION OF THE PREFERRED EMBODIMENTS

Figure 1:
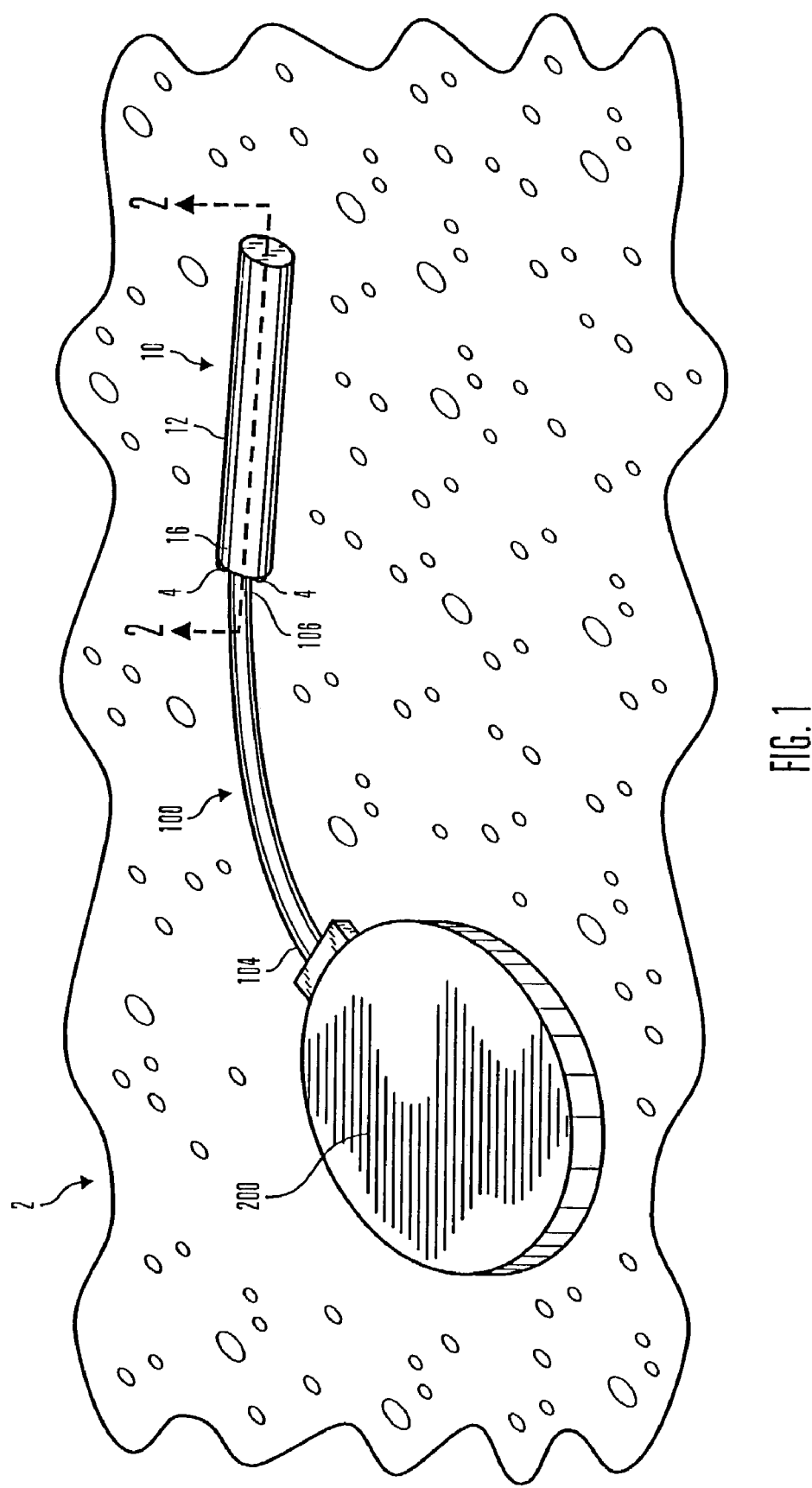
FIG. 1 is a perspective view of a reusable analyte sensor site and sensor monitor in accordance with an embodiment of the present invention.

As shown in the drawings for purposes of illustration, the invention is embodied in a reusable analyte sensor site that is used with a replaceable analyte sensor that determines body characteristics on a continuous, intermittent or near continuous basis. In preferred embodiments of the present invention, the replaceable analyte sensor is for determining glucose levels in the blood and/or bodily fluids of the user. However, it will be recognized that further embodiments of the invention may be used to determine the levels of other agents, characteristics or compositions, such as lactate, oxygen, hormones, cholesterol, medication concentrations, viral loads (e.g., HIV), or the like. The reusable analyte sensor site and replaceable analyte sensor are primarily adapted for use in sub-dermal or inter-peritoneal human tissue. However, still further embodiments may be placed in other types of tissue, such as muscle, lymph, organ tissue, veins, arteries or the like, and used in animal tissue. In other embodiments, the reusable analyte sensor site may be used with a medication or fluid infusion catheter, stimulator, pacing lead, or other medical device that requires regular replacement.

As shown in FIGS. 1-3, the reusable analyte sensor site 10 in accordance with preferred embodiments of the present invention includes a site housing 12 that is implanted in sub-dermal or inter-peritoneal tissue 2. Initially, the implanted site housing 12 is sutured in position by sutures (not shown). Preferably, the sutures are absorbable by the body. However, in alternative embodiments, the sutures are permanent.

In preferred embodiments, the material of the site housing 12 is formed to create an interior cavity 14 to support an ingrown and vascularized tissue (see FIGS. 2 and 3) structure around a replaceable analyte sensor 100. In addition to the interior cavity 14, the site housing 12 will form a conduit 16 that provides an entrance from the body tissue 2 to the interior cavity 14 of the site housing 12. The conduit 16 should be sized long enough so that the trauma associated with inserting and replacing the replaceable analyte sensor 100 (or catheter) will not affect the ingrown and vascularized tissue structure formed around the interior cavity 14 and an active sensing portion 102 of the replaceable analyte sensor 100 (or the outlet port of the replaceable catheter). Preferably, the length of the conduit is 5 millimeters. However, larger or smaller lengths (ranging from 2 millimeters to 20 millimeters or more) may be used with the selection being dependent on the size of the site housing 12, the type of tissue 2 the site housing 12 is implanted in, the frequency within which the replaceable analyte sensor 100 (or replaceable catheter, stimulator, pacing lead, or the like) must be replaced, or the like. Preferred embodiments of the site housing 12 can remain implanted in the tissue between 1 to 2 years. However, the actual long term life of the reusable analyte sensor site 10 will be a function of the material, the surface texture, the chemistry and the type of tissue 2 the reusable analyte sensor site 10 is implanted in. The goal is to achieve a reusable analyte sensor site 10 that is stable for multiple use to minimize the effects of frequent sensor replacement.

Preferably, the site housing 12 is formed from textured Teflon® or Dacron® that has a porosity selected to allow tissue ingrowth (i.e., cellular attachment) and vascularization of the material of the site housing 12. Many suitable materials are available from Gore & Associates Inc. and/or Baxter International. In alternative embodiments, other materials may be used, such as glass, sintered or woven metal meshes (e.g., titanium or other bio-compatible metal), composites, laminates, or the like, as long as they provide good vascularization and ingrowth of tissue. In preferred embodiments, the porosity (or mesh) size of the selected material is selected to be between 2-25 microns. However, in alternative embodiments, the porosity may be selected to be other sizes such that cells can attach and vascularization will occur. However, the porosity (or mesh) size must be selected to inhibit tissue ingress and keep tissue cells away from the active sensing portion 102 of the replaceable analyte sensor 100. Also, the sizing must be selected to avoid, or substantially minimize formation of a Fibrin sheath that attaches to the material of the site housing 12 or which causes encapsulation of the site housing 12. For example, as shown in FIG. 3, the porosity of the material of the site housing 12 is selected to promote cellular attachment of cells C to the mesh pores so as to encourage the vascularization of the site housing 12 with capillary vessels V to assure a good supply of bodily fluid F in and around the active sensing portion 102 of the replaceable analyte sensor 100 (or catheter), while at the same time inhibiting the ingress of tissues and cells C.

In addition to promoting tissue ingrowth and vascularization, the material used to form the site housing 12 must be sufficiently permeable to the analyte which is to be measured by the active sensing portion 102 of the replaceable analyte sensor 100. For instance, if glucose levels are being measured, the ingrown and vascularized site housing 12 must pass glucose (and transporting fluids) from the tissue 2 to the active sensing portion 102 of the replaceable analyte sensor 100 so that the glucose levels can be measured. Alternatively, if a replaceable catheter (not shown) is being used, such as for example to deliver insulin, the ingrown and vascularized site housing 12 must pass insulin out of the interior cavity 14 into the tissue 2. Further, if a replaceable stimulator or pacing lead (not shown) is being used, such as for example to deliver electrical pulses to the brain or heart, the ingrown and vascularized site housing 12 must pass electrical pulses out of the interior cavity 14. In particular embodiments, the material of the site housing 12 may also be selected to keep out certain materials or bodily fluid constituents that could interfere with or alter the readings of the active sensing portion 102 of the replaceable analyte sensor 100. It is further preferred that the material of the site housing 12 be selected so that any by products given off by the analyte sensing reaction will pass through the vascularized site housing and be removed by the body of the user. In alternative embodiments, the material of the site housing 12 will be selected to pass the analyte but to contain any materials, or by products, produced by the replaceable analyte sensor 100.

As shown in FIG. 2 the interior cavity 14 of the site housing 12 is selected to be sufficiently large to accommodate the active sensing portion 102 of the replaceable analyte sensor 100 (or replaceable catheter). However, the interior cavity 14 should not be so large that the fluid within the interior cavity 14 (i.e., passed through the vascularized site housing 12) becomes stagnant. It is important that the fluid within the interior cavity 14 change frequently to provide an accurate reading on the active sensing portion 102 of the replaceable analyte sensor 100.

In preferred embodiments of the present invention, the replaceable analyte sensor is a electrochemical sensor that uses either enzymatic or fluorescent techniques to determine the analyte level. In the illustrated embodiments, the active sensing portion 102 of the replaceable analyte sensor 100 is inserted through the conduit 16 of the site housing 12 and slid into the interior cavity 14 of the site housing 12 to take analyte level readings. A connection end 104 of the replaceable analyte sensor 100 is generally attached to an analyte monitor 200 that is implanted in the body tissues 2 of the user. Preferably, the analyte monitor 200 transmits the signal values, raw data, operational information and parameters, or the like, to an external information retrieving device (not shown) or another implanted medical device (not shown). In alternative embodiments, the analyte monitor 200 may be incorporated into an implantable medication (or fluid) delivery pump, such as discussed above. Although it is possible to have the connection end 104 of the replaceable analyte sensor 100 extend outside of the body, this approach is not preferred due to the risk of infection, irritation, the possible inconvenience of having external connections, or the like.

Once in place, the traumatized tissue 4 around the conduit entrance 22 will tend to attach and encapsulate the entrance 22 to the conduit 16 that opens out to the body tissue 2 and the mid-portion 106 of the replaceable analyte sensor 100 that is not within the interior cavity 14 of the site housing 12. This also tends to bind the entrance 22 of the conduit 16 to the mid-portion 106 of the replaceable analyte sensor 100. However, due to the length of the conduit 16 and the distance of the traumatized tissue 4 from the interior cavity 14, there is little, or no, trauma and encapsulation that will occur around the already established interior cavity 14 of the site housing 12. Thus, the active sensing portion 102 can begin to take readings relatively soon after implantation, stabilization and calibration of the replaceable analyte sensor 100. The entrance 22 of the conduit and the mid-portion 106 of the replaceable analyte sensor 100 that are encapsulated do not present an issue, since they do not affect operation of the active sensing portion 102 of the replaceable analyte sensor 100.

When the replaceable analyte sensor 100 is replaced, the encapsulation and tissue attachment 4 around the entrance 22 of the conduit 16 is cut to free the replaceable analyte sensor 100, after which the replaceable analyte sensor 100 is withdrawn from the conduit 16 and interior cavity 14 of the site housing 12. The removal process causes trauma around the entrance 22 of the conduit 16; however, it does not traumatize the interior cavity 14, since it is located a sufficient distance away from the entrance 22 of the conduit 16 to avoid the effects of the new trauma. After removal of the old replaceable analyte sensor 100, a new replaceable analyte sensor 100 is inserted through the conduit 16 and into the interior cavity 14 of the site housing 12.

As discussed, preferred embodiments of the replaceable analyte sensor 100 are electrochemical in nature. For instance, the sensor may use electrodes and glucose oxidase to measure the glucose levels in the bodily fluids. Examples of electrochemical sensors are shown and described in U.S. Pat. No. 5,391,250 to Cheney, II et al., entitled "Method of Fabricating Thin Film Sensors"; U.S. Pat. No. 5,390,671, to Lord et al., entitled "Transcutaneous Sensor Insertion Set"; U.S. Pat. No. 5,165,407, to Wilson et al., entitled "Implantable Glucose Sensor"; and U.S. Pat. No. 4,890,620, to Gough, entitled "Two-Dimensional Diffusion Glucose Substrate Sensing Electrode", which are incorporated herein in their entireties by reference. Alternative embodiments may utilize optical properties such as shown and described in U.S. Pat. No. 5,605,152, to Lord et al., entitled "Optical Glucose Sensor," or fiber optic structures and/or optical/fluorescent compounds such as shown and described in U.S. patent application Ser. No. 08/752,945 (corresponding to PCT/US 96/18720), to Van Antwerp et al., entitled "Detection of Biological Molecules Using Chemical Amplification and Optical Sensor," all of which are herein incorporated by reference. Other sensor technologies suitable for implantation and working with bodily fluids are acceptable for use with the reusable analyte sensor site 10.

In alternative embodiments, the replaceable analyte sensor does not need to extend outside and beyond the entrance 22 of the conduit 16. For instance, the replaceable analyte sensor may be in the form of a patch that is placed inside the interior cavity 14 and integrated by light transmitted through the skin. In this situation, the entrance 22 of the conduit 16 would be capped and uncapped to provide access to the replaceable analyte sensor and the interior cavity 14. In another alternative embodiment, the entrance 22 of the conduit 16 is covered by a pierceable septum, or the like, and analyte sensor material, such as contained in microspheres, gels, or the like, is injected through the conduit 16 into the interior cavity 14, and withdrawn (if necessary) by the same route when new sensor material is to be placed into the interior cavity 14.

Figure 4:
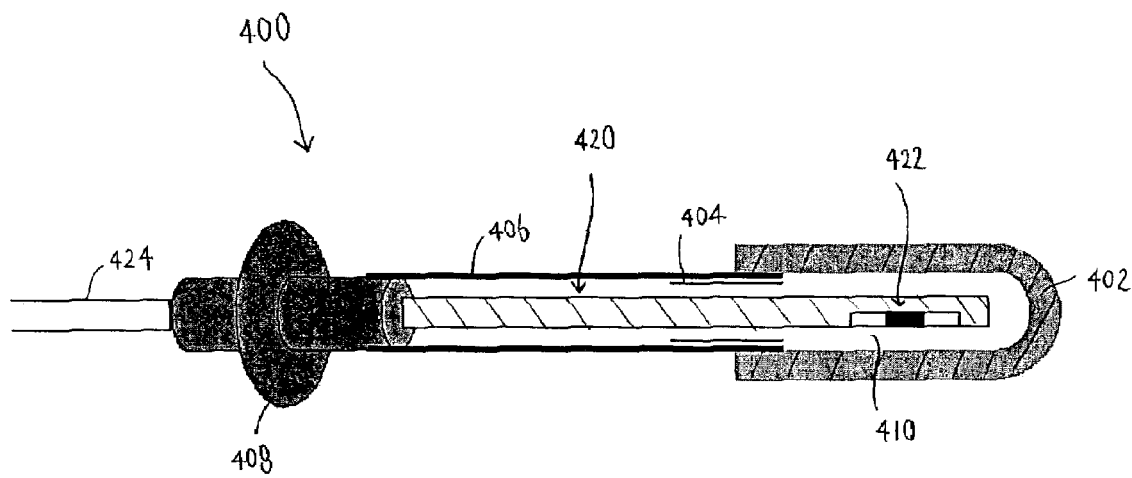
FIG. 4 is a partial cross-sectional view of a reusable analyte sensor site in accordance with another embodiment of the present invention.

In another embodiment of the present invention, the reusable analyte sensor site 400 includes a site housing 402, as illustrated in FIG. 4, that is implanted in peritoneal, subcutaneous, adipose, or the like tissue (not shown). The site housing 402 is preferably formed from material(s), such as polytetra fluoroethylene (PTFE) or the like, which promotes tissue attachment and vascularization and is also permeable to the analyte to be measured. For example, the site housing 402 may include an outer vascularizing membrane of PTFE and an inner cell-impermeable membrane of PTFE, such as that available from TheraCyte, Inc. Alternatively, the site housing 402 may be formed from any of the other material(s) used to form the site housing 12 shown and described above in the embodiments of FIGS. 1-3. In further alternative embodiments, the site housing 402 may be formed from material(s) that is not subject to vascularization or tissue attachment and encapsulation, such as porous polyurethane, porous silicone, silicone foam, or the like. The site housing 402 forms an interior cavity 410 for insertion of the replaceable analyte sensor 420 (or replaceable catheter, stimulator, pacing lead, or the like), and includes a loading port 404 for insertion of the sensor 420 into the interior cavity 410 of the site housing 402.

The sensor site 400 may additionally include a tube 406 that is connected to one end of the site housing 402, and is preferably formed from a biocompatible material, such as polyethylene, silicone, or the like. The sensor site 400 may further include a sealing member 408 that is connected to the other end of the tube 406 for sealing the tube 406 and the site housing 402 against the entry of any materials, cells, or bodily fluid constituents that could interfere with or alter the readings of the sensor 420. In the illustrated embodiment, the sealing member 408 is a suture disc, sleeve, or tab 408, which includes a resealable opening or insertion site (such as the insertion site 440 shown in FIG. 6) for insertion of the sensor 420 into the tube 406 and the site housing 402. In particular embodiments, the suture disc 408 may also include suture tabs (such as the suture tabs 432 shown in FIGS. 6 and 9) for attaching the tube 406 in position to the body tissue of the patient by sutures (not shown), and the site housing 402 rests at the desired location in the peritoneal, subcutaneous, adipose, or the like tissue. For example, the tube 406 may be secured in position by suturing the suture disc 408 to muscle tissue, and the site housing 402 may rest at the desired location in the peritoneal cavity.

Figure 5:
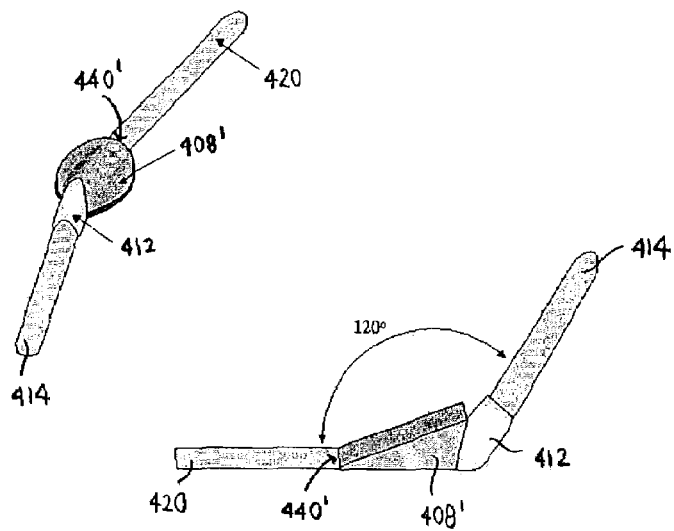
FIG. 5 is a perspective view of an analyte sensor and sewing cuff for a reusable analyte sensor site in accordance with an embodiment of the present invention.

In other embodiments, the sealing member may be a sewing cuff 408', as shown in FIG. 5, which includes a resealable opening or insertion site 440' for insertion of the sensor 420 into the tube 406 and the site housing 402. One end 414 of the sewing cuff 408' is connected to the tube 406, and the tube 406 may be secured in position by suturing the sewing cuff 408' to the body tissue of the patient, with the site housing 402 resting at the desired location in the peritoneal, subcutaneous, adipose, or the like tissue. The sewing cuff 408' may also include an angled fitting 412 for adjusting the angle of the sensor 420 relative to the suture location. In the illustrated embodiment, the angle of the fitting 412 is 120 degrees; however, in alternative embodiments, the angle may be greater or less than 120 degrees, depending on the type of patient. In further alternative embodiments, the sealing member may be any structure that includes a resealable opening and is capable of sealing the sensor 420 within the tube 406 and the site housing 402. Additionally, the suture disc 408 or sewing cuff 408' may be placed over the sensor 420 at a location away from the sealing member, and utilized to secure the tube 406 in position to the body tissue of the patient, with the site housing 402 resting at the desired location in the peritoneal, subcutaneous, adipose, or the like tissue.

In preferred embodiments, the sensor 420 includes an active sensing portion or sensing element 422, and a sensor lead 424 for connecting the sensor 420 to an implantable unit. The sensor 420 may generally be of the type described in U.S. patent application Ser. No. 10/036,093, filed Dec. 28, 2001 and entitled "Sensing Apparatus and Process," which is herein incorporated by reference. Additionally, methods for implanting and connecting the sensor 420 with the implantable unit are further described in U.S. patent application Ser. No. 10/034,627, filed Dec. 27, 2001 and entitled "Method and System for Non-Vascular Sensor Implantation," and Provisional Application Ser. No. 60/414,290, filed Sep. 27, 2002 and entitled "Implantable Sensor Method and System," both of which are herein incorporated by reference. The sensor lead 424 is connected to an implantable unit (not shown) located in the body tissue of the user, such as the analyte monitor 200 shown and described above in the embodiments of FIGS. 1-3, or an implantable medication (or fluid) delivery pump. The implantable unit is preferably located away from the sensor site 400. For example, the site housing 402 may be implanted in the peritoneal cavity, and the implantable unit may be located in subcutaneous tissue. In alternative embodiments, the implantable unit may be located near the sensor site 400. In further alternative embodiments, the sensor lead 424 may extend outside the body, and connect to an analyte monitor, medication (or fluid) delivery pump, or other medical device located outside the body of the user. In other embodiments, if a replaceable stimulator (not shown) is inserted into the site housing 402, the stimulator may be connected to a lead that is implanted in the brain, and the stimulator may be implanted in the subcutaneous tissue. Alternatively, if a replaceable pacing lead (not shown) is inserted into the site housing 402, the pacing lead may be connected to a pacemaker that is implanted in the subcutaneous tissue, and the pacing lead may be implanted in heart tissue.

The tube 406 is secured to the site housing 402, in order to seal the interior cavity 410 and prevent the entry of any materials, cells, or bodily fluid constituents that could interfere with or alter the readings of the active sensing portion 422 of the replaceable analyte sensor 420. The suture disc 408 (or sewing cuff 408') is also secured to the tube 406, in order to seal the tube 406 and prevent the entry of any such materials, cells, or bodily fluid constituents. In particular embodiments, a silicone rubber (e.g., Med-A) or other adhesive may be applied at the junction between the tube 406 and the site housing 402, and at the junction between the suture disc 408 and the tube 406. In other particular embodiments, a compression seal may be used to secure the tube 406 to the site housing 402, as well as to secure the suture disc 408 to the tube 406. For example, an O-ring (not shown) may be placed over the junction between the tube 406 and the site housing 402. Also, the tube 406 may be undersized relative to the suture disc 408 such that the tube 406 tightly fits around and "squeezes" the suture disc 408 to seal the junction between the suture disc 408 and the tube 406. In still other particular embodiments, ultraviolet, heat, or other energy may be utilized to secure the tube 406 to the site housing 402, and to secure the suture disc 408 to the tube 406. In yet other particular embodiments, a chemical adhesive may be applied at the junction between the tube 406 and the site housing 402, and at the junction between the suture disc 408 and the tube 406, and then cured with ultraviolet, heat, or other energy.

In alternative embodiments, the site housing 402, tube 406, and/or suture disc 408 (or sewing cuff 408') may be molded together using a single mold or a series of molds. For example, referring to FIGS. 6 and 9, the tube 406' and suture disc 408" may be molded together as an integral tube/disc piece 430, which may then be secured to the site housing 402' using an overmold or compression seal. In particular embodiments, the tube/disc piece 430 may be undersized relative to the loading port 404' such that the tube/disc piece 430 tightly fits around and "squeezes" the loading port 404' to seal the junction between the loading port 404' and the tube/disc piece 430. In other particular embodiments, an O-ring (not shown) may be placed over the junction between the tube/disc piece 430 and the site housing 402'. In further alternative embodiments, the site housing 402, tube 406, and/or suture disc 408 (or sewing cuff 408') may be separately molded, and then connected together using silicone rubber (e.g., Med-A), chemical, and/or any other appropriate adhesive(s), and/or ultraviolet, heat, or the like energy, as described above in the embodiments of FIGS. 4 and 5. For example, a silicone rubber (e.g., Med-A) or other adhesive may be applied at the junction between the tube/disc piece 430 and the site housing 402' shown in FIG. 6 to secure the tube/disc piece 430 to the site housing 402', rather than utilizing the compression seal illustrated in FIG. 6.

The replaceable analyte sensor 420 is inserted through a resealable opening or insertion site (such as the insertion site 440 shown in FIG. 6 or insertion site 440' shown in FIG. 5) formed in the suture disc 408 (or sewing cuff 408') and into the tube 406, in order to position the active sensing portion 422 of the sensor 420 in the site housing 402 to take analyte level readings. The insertion site 440 is preferably located in the subcutaneous tissue of the patient, and may be accessed from the exterior of the patient's body utilizing a biopsy trocar (such as the biopsy trocar 454 shown in FIG. 7) or other device for introducing the sensor 420 through the insertion site 440 formed in the suture disc 408 (or sewing cuff 408') and into the tube 406 and the site housing 402. Such a biopsy trocar may generally be of the type shown and described in U.S. patent application Ser. No. 10/034,627, filed Dec. 27, 2001 and entitled "Method and System for Non-Vascular Sensor Implantation," and Provisional Application Ser. No. 60/414,290, filed Sep. 27, 2002 and entitled "Implantable Sensor Method and System," both of which are herein incorporated by reference.

Figure 6:
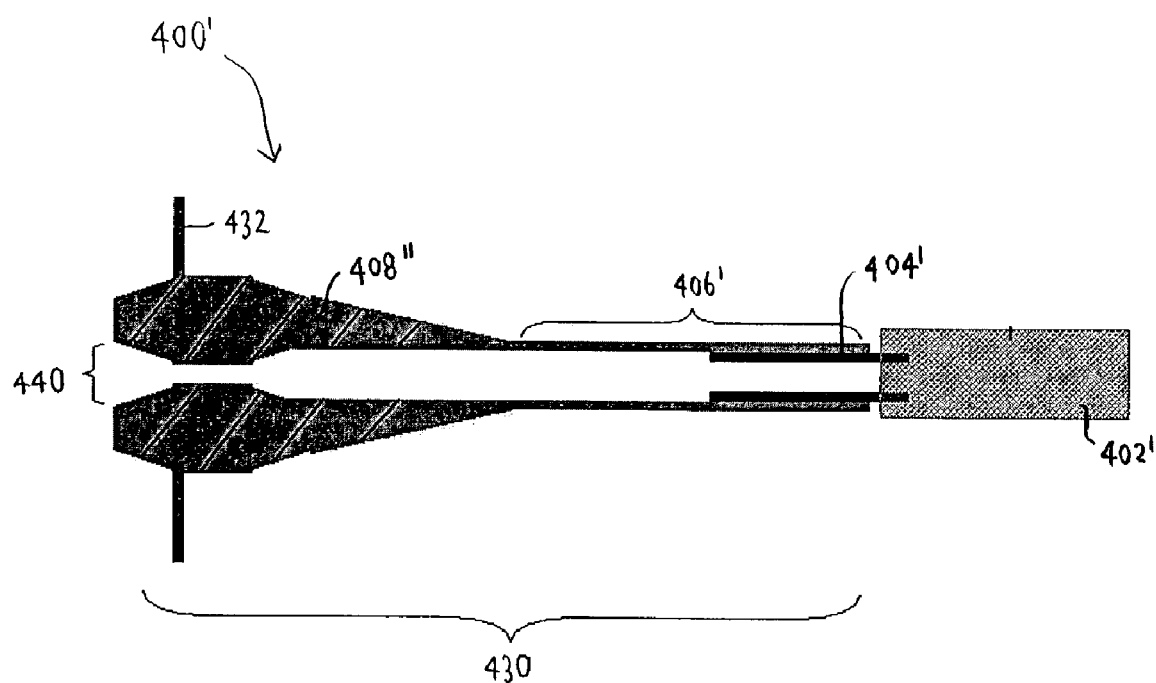
FIG. 6 is a partial cross-sectional view of a reusable analyte sensor site in accordance with yet another embodiment of the present invention.
Figure 7:
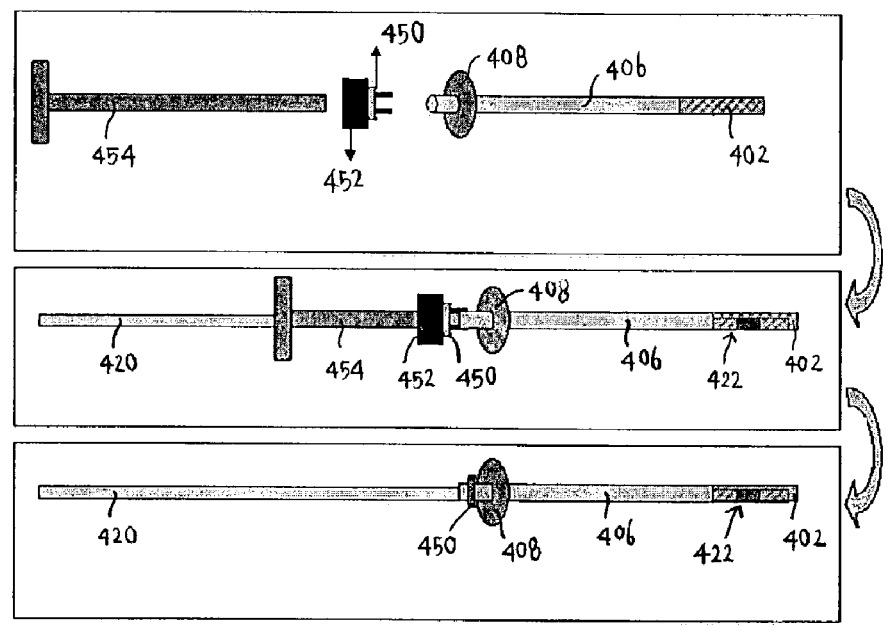
FIG. 7 is a perspective view of a biopsy trocar for replacing an analyte sensor in a reusable analyte sensor site in accordance with an embodiment of the present invention.
Figure 9:
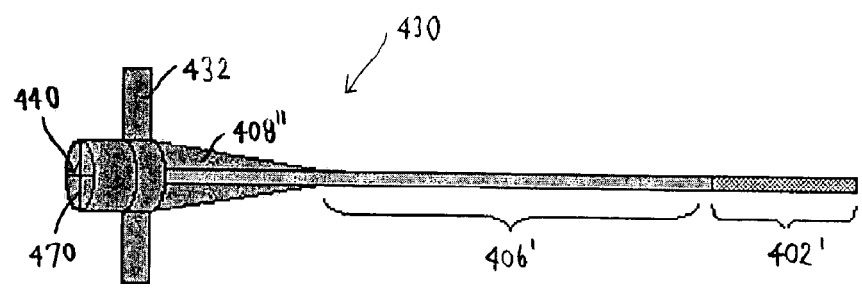
FIG. 9 is an enlarged perspective view of a reusable analyte sensor site in accordance with an embodiment of the present invention.

After insertion of the sensor 420 through the insertion site 440 formed in the suture disc 408 (or sewing cuff 408') and into the tube 406 and the site housing 402, and placement of the active sensing portion 422 of the sensor 420 in the site housing 402, the insertion site 440 is sealed around the sensor 420. The suture disc 408 (or sewing cuff 408') and tube 406 thus provide a resealable insertion site for replacement of the sensor 420. In preferred embodiments, a compression seal is used to seal the insertion site 440. In particular embodiments, the insertion site 440 in the suture disc 408" may be undersized relative to the sensor 420 such that the insertion site 440 tightly fits around and "squeezes" the sensor 420 to seal the junction between the sensor 420 and the insertion site 440, as shown in FIG. 6. In other particular embodiments, an O-ring 450 may be placed over the suture disc 408 to create the compression seal in order to seal the insertion site 440, as shown in FIG. 7. For example, the biopsy trocar 454 and an O-ring introducer 452 may used to place the O-ring 450 over the suture disc 408. In further particular embodiments, a cross-cut 470 may be made at the insertion site 440, which provides a permanent compression seal in order to seal the insertion site 440, as shown in FIG. 9.

Figure 8:
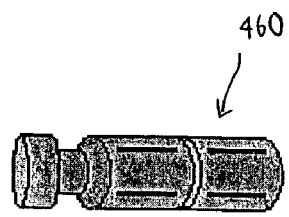
FIG. 8 is an enlarged perspective view of a modified Touhy-Borst for use with a reusable analyte sensor site in accordance with an embodiment of the present invention.
Figure 10:
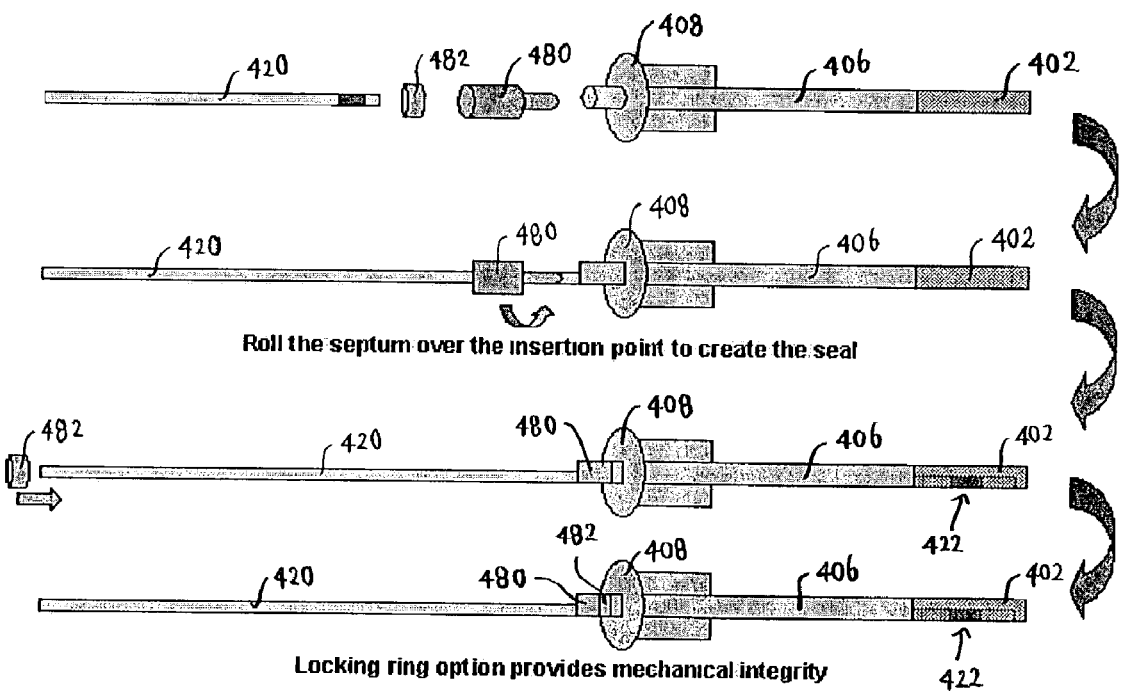
FIG. 10 is an enlarged perspective view of a replaceable septum and optional locking ring for use with a reusable analyte sensor site in accordance with an embodiment of the present invention.

In alternative embodiments, a mechanical seal may be utilized to seal the insertion site 440 around the sensor 420. In particular alternative embodiments, a luer fitting (not shown) may be placed over the sensor 420 and locked into the insertion site 440. In other alternative embodiments, a standard or modified Touhy-Borst 460, as shown in FIG. 8, may be placed over the sensor 420, and then turned to lock the sensor 420 into the insertion site 440. For example, the modified Touhy-Borst 460 may be designed such that one turn in one direction of the Touhy-Borst 460 locks the sensor 420 into the insertion site 440, and one turn of the Touhy-Borst 460 in the opposite direction unlocks the sensor 420 from the insertion site 440. In further alternative embodiments, the seal may be replaced upon insertion of a new sensor 420, as shown in FIG. 10. A replaceable septum 480 may be placed over the sensor 420 and into the insertion site 440. The septum 480 is then rolled over the insertion site 440 to create the required seal. An optional locking ring 482 may then be placed over the septum 480 for additional mechanical strength. In still other alternative embodiments, tools (e.g., insertion guns) may be used to insert and lock the sensor 420 into the insertion site 440 in order to seal the insertion site 440.

Once in place, the patient's body vascularizes, and tissue attaches to, the implanted site housing 402 and tube 406 with the sensor 420 sealed therein. In preferred embodiments, the sensor 420 may be easily replaced within the site housing 402. When the sensor 420 is replaced, the insertion site 440 is unsealed to free the sensor 420. For example, in embodiments utilizing a compression seal at the insertion site 440, the insertion site 440 may be unsealed by inserting a biopsy trocar or other introducing device (such as the biopsy trocar 454 shown in FIG. 7) into the insertion site 440, or by removing the O-ring 450 placed around the suture disc 408 shown in FIG. 7. In other embodiments utilizing a mechanical seal at the insertion site 440, the insertion site 440 may be unsealed by turning the Touhy-Borst 460 shown in FIG. 8 to unlock the sensor 420 from the insertion site 440, or by removing the replaceable septum 480 and optional locking 482 placed around the suture disc 408 shown in FIG. 10. Once the insertion site 440 is unsealed, the old sensor 420 is withdrawn from the site housing 402 and the tube 406. A new sensor 402 is then inserted through the insertion site 440 and into the tube 406 and the interior cavity 410 of the site housing 402, and the insertion site 440 is resealed around the sensor 420. Thus, the sensor 420 is easily replaced within the site housing 402, without traumatizing any of the vascularization around the site housing 402 and tube 406, and without requiring any cutting of the tissue encapsulating the site housing 402 and tube 406.

Figure 11:
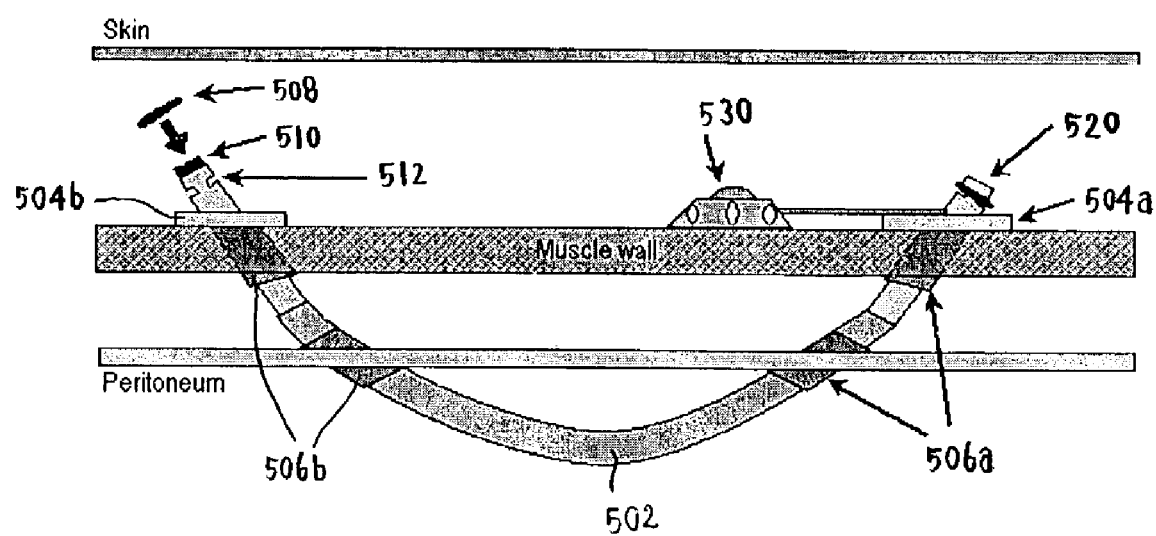
FIG. 11 is a perspective view of a reusable analyte sensor site in accordance with still another embodiment of the present invention.

In accordance with yet another embodiment of the present invention, the reusable analyte sensor site 500 includes a site housing 502 that is implanted in the peritoneal tissue of the patient, as illustrated in FIG. 11. Alternatively, the site housing 502 may be implanted in subcutaneous, adipose, or the like tissue of the patient. The replaceable analyte sensor is inserted into the site housing 502 to take analyte level readings. The sensor site 500 may also include growth cuffs 506a and 506b that are secured to each end of the site housing 502 in a manner similar to that for securing the tube 406 to the site housing 402 shown and described above in the embodiments of FIGS. 4-10. The sensor site 500 may further include suture discs or sleeves 504a and 504b that are attached to the growth cuffs 506a and 506b in a manner similar to that for securing the suture disc 408 to the tube 406 shown and described above in the embodiments of FIGS. 4-10. The suture discs 504a and 504b may include suture tabs (such as the suture tabs 432 shown in FIGS. 6 and 9) for attaching each end of the site housing 502 to the muscle tissue of the patient by sutures (not shown), and the site housing 502 rests at the desired location in the peritoneal tissue. At one end, the suture disc 504a includes an insertion site 520 for easily inserting and replacing the sensor in a manner similar to that shown and described above in the embodiments of FIGS. 4-10. At the other end, the suture disc 504b has a sealed end 510, and a seat 512 for receiving an O-ring 508 that is placed over the suture disc 504b to strengthen the seal. The advantage of this configuration is that the position of the sensor in the site housing 502 is generally known at all times.

In particular embodiments, an injection site 530 may be connected to the sensor site 500 so that the site housing 502 may be flushed upon implantation of the site housing 502, after removal of an old sensor and prior to replacement of a new sensor, or the like. The injection site 530 may be formed from soft silicone or any other appropriate material, and may be catheterized to the sensor site 500 to provide access to the site housing 502. Antibiotics, saline, or a combination of any appropriate solution or drug may be infused through the injection site 530 and into the site housing 502. This feature creates a way of accessing the site housing 502 in case of an infection. In alternative embodiments, the injection site 530 may be included directly in the sensor site 500. For example, the suture disc 504a may include the insertion site 520 for the sensor and an additional insertion site(s) for infusion of fluids. Alternatively, the suture disc 504a may include a single insertion site for a multilumen catheter that provides at least one lumen for inserting the sensor and at least one lumen for infusing fluids.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A reusable analyte sensor site for use with a replaceable analyte sensor for determining a level of an analyte in a patient, the site comprising:
    a site housing material formed to have an interior cavity with an opening, wherein the site housing material is selected to promote tissue ingrowth and vascularization and be free of tissue ingress, and wherein the site housing material permits fluid including the analyte to pass through the site housing material to the interior cavity to permit measurement by the replaceable analyte sensor; and
    a resealable insertion site coupled to one end of the site housing material for inserting the replaceable analyte sensor into the interior cavity of the site housing material, the resealable insertion site comprising:
        a tube having a first end and a second end, wherein the first end of the tube is coupled to one end of the site housing material; and
        a sealing member having a resealable opening, wherein the second end of the tube is coupled to the sealing member such that the tube is coupled between the site housing material and the sealing member;
        wherein the replaceable analyte sensor is inserted through the resealable opening, and the resealable opening is sealed upon placement of the replaceable analyte sensor within the interior cavity of the site housing material.

2. A site according to claim 1, wherein the sealing member is a suture disc for attaching the tube to body tissue of the patient.

3. A site according to claim 2, wherein the tube and the suture disc are combined into an integral unit.

4. A site according to claim 2, further comprising another suture disc coupled to the other end of the site housing material for attaching the other end of the site housing material to the body tissue of the patient.

5. A site according to claim 1, wherein the sealing member is a sewing cuff for attaching the tube to body tissue of the patient.

6. A site according to claim 1, wherein the resealable opening is sealed using a compression seal.

7. A site according to claim 6, wherein the tube has a smaller size than the sealing member such that the tube compresses the sealing member within the tube and seals the resealable opening round the replaceable analyte sensor.

8. A site according to claim 6, wherein the resealable insertion site further includes a ring placed over the sealing member to compress and seal the resealable opening round the replaceable analyte sensor.

9. A site according to claim 6, wherein a cross-cut is formed in the sealing member at the resealable opening.

10. A site according to claim 1, wherein the resealable opening is sealed using a mechanical seal.

11. A site according to claim 10, wherein the resealable insertion site further includes a Touhy-Borst placed over the sensor to lock the replaceable analyte sensor into the resealable opening.

12. A site according to claim 10, wherein the resealable insertion site further includes a replaceable septum placed over the sensor and the resealable opening.

13. A site according to claim 1, wherein the sensor site is adapted for connection to an injection site for delivering fluids into the site housing material.

14. A site according to claim 1, wherein the site housing material is for implantation into inter-peritoneal tissue of the patient, and the resealable insertion site is for implantation into subcutaneous tissue of the patient.

15. A site according to claim 1, wherein the site housing material is selected from a group of materials consisting essentially of polytetra fluoroethylene, porous polyurethane, porous silicone, and silicone foam.

16. A site according to claim 1, wherein the site housing will last for a period of time such that it can be used with two or more consecutive replaceable analyte sensors.

17. A site according to claim 1, wherein the site housing material passes glucose, and wherein the replaceable analyte sensor is a glucose sensor.

18. A site according to claim 1, wherein the interior cavity has a predetermined size to inhibit stagnation of the fluid including the analyte within the interior cavity.

19. A system for measuring analyte in a body of a patient, the system comprising:
    a replaceable analyte sensor for determining a level of an analyte; and
    a reusable analyte sensor site including:
        a site housing material fanned to have an interior cavity with an opening, wherein the site housing material is selected to promote tissue ingrowth and vascularization and be free of tissue ingress, and wherein the site housing material permits fluid including the analyte to pass through the site housing material to the interior cavity to permit measurement by the replaceable analyte sensor; and
        a resealable insertion site coupled to the site housing material for inserting the replaceable analyte sensor into the interior cavity of the site housing material, the resealable insertion site comprising:

a tube having first end and a second end, wherein the first end of the tube is coupled to one end of the site housing material; and a sealing member having a resealable opening, wherein the second end of the tube is coupled to the sealing member such that the tube is coupled between the site housing material and the sealing member;

wherein the replaceable analyte sensor is inserted though the resealable opening, and the resealable opening is sealed neon placement of the replaceable analyte sensor within the interior cavity of the site housing material.

20. A system according to claim 19, wherein the sealing member is a suture disc for attaching the tube to body tissue of the patient.

21. A system according to claim 20, wherein the tube and the suture disc are combined into an integral unit.

22. A system according to claim 20, wherein the reusable analyte sensor site further includes another suture disc coupled to the other end of the site housing material for attaching the other end of the site housing material to the body tissue of the patient.

23. A system according to claim 19, wherein the sealing member is a sewing cuff for attaching the tube to body tissue of to patient.

24. A system according to claim 19, wherein the resealable opening is sealed using a compression seal.

25. A system according to claim 24, wherein the tube has a smaller size than the sealing member such that the tube compresses the sealing member within the tube and seals the resealable opening around the replaceable analyte sensor.

26. A system according to claim 24, wherein the resealable insertion site further includes a ring placed over the sealing member to compress and seal the resealable opening around the replaceable analyte sensor.

27. A system according to claim 24, wherein a cross-cut is formed in the sealing member at the resealable opening.

28. A system according to claim 19, wherein the resealable opening is sealed using a mechanical seal.

29. A system according to claim 28, wherein the resealable insertion site further includes a Touhy-Borst placed over the sensor to lock the replaceable analyte sensor into the resealable opening.

30. A system according to claim 28, wherein the resealable insertion site further includes a replaceable septum placed over the sensor and the resealable opening.

31. A system according to claim 19, wherein the reusable analyze sensor site is adapted for connection to an injection site for delivering fluids into the site housing material.

32. A system according to claim 19, wherein the site housing material is for Implantation into inter-peritoneal tissue of the patient, and the resealable insertion site is for implantation into subcutaneous tissue of the patient.

33. A system according to claim 19, wherein the site housing material is selected from a group of materials consisting essentially of polytetra fluoroethylene, porous polyurethane, porous silicone, and silicone foam.

34. A system according to claim 19, wherein the site housing will last for a period of time such that it can be used with two or more consecutive replaceable analyte sensors.

35. A system according to claim 19, wherein the site housing material passes glucose, and wherein the replaceable analyze sensor is a glucose sensor.

36. A system according to claim 19, wherein the interior cavity has a predetermined size to inhibit stagnation of the fluid including the analyte within the interior cavity.

* * * * *